United States Patent
Hasegawa

(10) Patent No.: US 8,983,029 B2
(45) Date of Patent: Mar. 17, 2015

(54) RADIOGRAPHIC APPARATUS AND METHOD FOR THE SAME

(71) Applicant: Naoki Hasegawa, Kyoto (JP)

(72) Inventor: Naoki Hasegawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 157 days.

(21) Appl. No.: 13/774,132

(22) Filed: Feb. 22, 2013

(65) Prior Publication Data

US 2014/0241496 A1 Aug. 28, 2014

(51) Int. Cl.
*A61B 6/00* (2006.01)
*G01N 23/04* (2006.01)
*G06T 5/00* (2006.01)
*G06T 5/10* (2006.01)

(52) U.S. Cl.
CPC ............... *G01N 23/04* (2013.01); *G06T 5/003* (2013.01); *G06T 5/10* (2013.01); *G06T 2207/10116* (2013.01); *G06T 2207/20056* (2013.01); *A61B 6/4035* (2013.01)
USPC .............. 378/62; 378/207; 382/132; 382/275

(58) Field of Classification Search
USPC ..................... 378/62, 98.8, 207; 382/132, 275
See application file for complete search history.

(56) References Cited

U.S. PATENT DOCUMENTS

| 2003/0016854 A1* | 1/2003 | Inoue et al. ................... 382/132 |
| 2011/0038522 A1* | 2/2011 | Baba ............................. 382/132 |
| 2012/0241629 A1* | 9/2012 | Kuwabara ..................... 250/362 |
| 2014/0050300 A1* | 2/2014 | Hasegawa ....................... 378/62 |

FOREIGN PATENT DOCUMENTS

| JP | 2008-220657 | 9/2008 |
| JP | 2012-50771 | 3/2012 |

* cited by examiner

*Primary Examiner* — Glen Kao
(74) *Attorney, Agent, or Firm* — Andrew F. Young, Esq.; Lackenbach Siegel, LLP

(57) ABSTRACT

An apparatus, system, and method corrects line deficiency in radiographic systems. A Fourier transform element provides a one-dimensional Fourier transform on a line orthogonal to a line of a moire patterns appearing in an X-ray image during a use. A peak frequency detection element detects the peak frequency indicating the spatial frequency of the moire pattern on the basis of the results of one-dimensional Fourier transform. The detected peak frequency is transformed to a number of pixels in 1 cycle of the moire pattern by a pixel cycle conversion element. The line deficiency correction element obtains pixels of the same phase as the line deficiency pixel in the moire pattern from the number of pixels, and then corrects the line deficiency pixel by using the pixel value thereof. Since the number of pixels in 1-cycle is acquired from the moire pattern in the X-ray image, the line deficiency can be corrected.

12 Claims, 13 Drawing Sheets

Fig. 5

| Peak frequency Pk | Number of pixels at 1 cycle Px (How many pixels in 1 cycle) |
|---|---|
| ⋮ | ⋮ |
| 1.3 | 5 |
| 1.4 | 9 |
| 1.5 | 9 |
| 1.6 | 4 |
| 1.7 | 4 |
| 1.8 | 7 |
| 1.9 | 7 |
| ⋮ | ⋮ |

35

RADIOGRAPHIC APPARATUS AND METHOD FOR THE SAME

CROSS REFERENCE TO RELATED APPLICATIONS

This application relates to JP Ser. No. 2010-197590, filed Sep. 3, 2010, the entire contents of which are incorporated herein fully by reference.

FIGURE SELECTED FOR PUBLICATION

FIG. 2

DESCRIPTION OF THE INVENTION

1. Technical Fields

The present invention relates to a radiographic apparatus that takes an X-ray image of a subject by using an X-ray grid that eliminates scattered radiations.

2. Description of the Related Art

A conventional radiographic apparatus takes an X-ray image by detecting the transmissive radiation through the subject to which X-ray is irradiated. But when the X-ray transmits through the subject, a scattered radiation occurs. When the radiophotographic image including the scattered radiation is taken, the X-ray image becomes blur and unclear. Therefore, an X-ray grid is arranged in the incident X-ray side of an X-ray detector to eliminate the scattered radiation through the subject. The X-ray grid is composed of an absorbent (e.g. lead) that absorbs X-ray and a transmission material (e.g. aluminum or air) that transmits X-rays one after the other a in parallel setting. The absorbent absorbs the scattered X-ray and only the X-rays transmitted along the transmission material in between the absorbents can be detected by the X-ray detector. Whereby the scattered rays are eliminated and the clear X-ray image can be obtained.

When an X-ray image of the subject, however, is taken by using an X-ray grid; a moire pattern appears in the obtained X-ray image due to the difference between the resolution of the X-ray detector and the density of the X-ray grid. Now, a resolution of X-ray detector, a density of X-ray gird, and a moire pattern are shown as a spatial frequency "lp/mm". The identifier "lp/mm" is called as line-ampere/millimeter and indicates how many pairs of black-and-white line are in 1 millimeter. The density of X-ray grid indicates how many pairs of an absorbent and a transmission material are in 1 millimeter or how many absorbents are in 1 millimeter. The resolution of X-ray detector indicates a spatial frequency of distinguishable limit, and if a pixel pitch is d, it is expressed as ½d. Then, the moire pattern indicates how many cycles of the wave pattern (line) are in millimeter.

On the other hand, in a traditional radiographic apparatus, if there is a line deficiency in a vertical (perpendicular) direction and a moire pattern of which lines are in near vertical direction appears, correction of the line deficiency is conducted by using the pixel value of every 4 adjacent pixels in right-and-left sides in horizontal (lateral) direction (For example, Patent document 1). A pixel value of every 4 adjacent pixels in right-and-left sides in the horizontal direction is used for a line deficiency pixel because the wave pattern of the moire pattern is composed of 1 cycle by 4 pixels. In addition, if no moire pattern appears in an X-ray image, a correction of the normal line deficiency is conducted by using the pixel value of every 1 adjacent pixel in right-and-left direction in the horizontal direction. Further, the line deficiency expresses that plural deficiency pixels occur in a line, but the line deficiency pixels in the present description are deficiency pixels comprising a line deficiency.

PRIOR ART DOCUMENTS

Patent Document

Patent Document: JP A2008-220657

ASPECTS AND SUMMARY OF INVENTION

Problems to be Solved by the Invention

There are a number of problems using conventional radiographic apparatuses, at least one of which this invention seeks to cure. Thus, one aspect of the present invention is to provide a radiographic apparatus that can precisely correct line deficiency. Specifically, the density of X-ray grid includes some errors due to such as production thereof and even if an X-ray grid having the same density labeling is employed, correction of the line deficiency may not be accurate. Further, even if an X-ray grid having the different density is employed, such correction may also not be accurate. In these cases, as the wave pattern of the moire pattern is not composed of 1 cycle by 4 pixels, the line deficiency cannot be accurately corrected.

For example, when an X-ray detector having the resolution 3.3 [lp/mm] (pixel pitch 0.15 mm) and an X-ray grid having 5 [lp/mm] are employed, a moire pattern appears in the X-ray image due to the reciprocal of frequency because, in this case, the density of the X-ray grid has a higher frequency than the resolution of the X-ray detector. Specifically, as shown in FIG. 11, when a pattern of the X-ray grid having the density of 5 [lp/mm] that is a higher frequency than the resolution of 3.3 [lp/mm] of the X-ray detector is sampled, the X-ray detector cannot accurately reproduce the pattern of the X-ray grid. Accordingly, the moire pattern that is a non-existing image having a spatial frequency, as the center of 3.3 [lp/mm], at the reciprocal and symmetrical position in which the density of the X-ray grid is 5 [lp/mm] appears in the X-ray image. Accordingly, as shown in FIG. 11, a difference between the density [lp/mm] of the X-ray grid and the resolution [lp/mm] of the X-ray detector is obtained, and then the spatial frequency of the moire pattern appeared at the reciprocal position can be calculated by subtracting the obtained difference thereof from the resolution [lp/mm] of the X-ray detector. Specifically, the spatial frequency of the moire pattern should be calculated as 3.3 [lp/mm]−(5 [lp/mm]−3.3 [lp/m])=1.6 [lp/mm].

When a moire pattern having the spatial frequency of 1.6 [lp/mm] appears in the X-ray image, it becomes the moire pattern of 1 cycle by 4 pixels as shown in FIG. 12. However, given an error of not less than 5% for the X-ray grid's density of 5 [lp/mm] exists and when, for example, the density is 4.7 [lp/mm], the spatial frequency [lp/mm] of the moire pattern should be a different one. Specifically, the spatial frequency is calculated as 3.3 [lp/mm]−(4.7 [lp/mm]−3.3 [lp/mm])=1.9 [lp/mm], and the moire pattern having the spatial frequency of 1.9 [lp/mm] appears in the X-ray image. Then, as shown in FIG. 13, it is understood that the moire pattern has 1 cycle by 7 pixels (actually 1 cycle by 3.5 pixels) instead of 1 cycle by 4 pixels. For example, when the actual density is 4.7 [lp/mm] due to an error, e.g. a manufacturing error, despite employing the X-ray grid labeled as the same density of 5 [lp/mm], even if a pixel value of every 4 adjacent pixels in right-and-left sides of a horizontal direction is employed as the line deficiency pixel, the correction may not be accurately conducted because the wave pattern of the moire pattern has 1 cycle by 7 pixels. As results, the wave pattern of the moire pattern after correction remains as disturbed at a part of the line deficiency pixels thereof.

Considering the above problems, one purpose of the present invention is to provide a radiographic apparatus that can accurately correct a line deficiency even if an X-ray grid including an error or an X-ray grid having a different density is employed. Another optional purpose of the present invention is to provide a method for operating such an apparatus for resolution of at least one of the concerns noted.

Means for Solving the Problem

The present invention comprises the following constitution to solve the above mentioned problems. Specifically, a radiographic apparatus or system according to the present invention comprises; a X-ray irradiation element that irradiates an X-ray to a subject; a X-ray detector that is operative to detect the X-rays passed through the subject; an X-ray grid arrayed in a X-ray incident side of the X-ray detector, which is operative to eliminate a scattering radiation; and further the radiographic apparatus is operative to take an X-ray image based on the X-ray detected by the X-ray detector and comprise; a Fourier transform element that conducts one-dimensional Fourier transform on a line orthogonal to a line of a moire pattern appearing in the X-ray image; a peak frequency detection element that detects a peak frequency based on the result of the one-dimensional Fourier transform; a pixel cycle conversion element that converts the peak frequency to a number of pixels in 1 cycle of the moire pattern; and a line deficiency correction element that obtains pixels in the same phase as the line deficiency pixel in the moire pattern from the number of pixels in 1 cycle of the moire pattern, whereby the correction of the line deficiency pixel by using the pixel value is operative.

According to another aspect of radiographic apparatus and system of the present invention, the invention further includes a Fourier transform element that conducts one-dimensional Fourier transform on a line orthogonal to a line of a moire pattern appeared in an X-ray image, and a peak frequency detection element that detects a peak frequency based on the result of the one-dimensional Fourier transform. The detected peak frequency is converted to a number of pixels in 1 cycle of the moire pattern by a pixel cycle conversion element. Then, a line deficiency correction element obtains pixels in the same phase as the line deficiency pixels in the moire pattern from the number of pixels in 1 cycle of the moire pattern, and then corrects the line deficiency pixel by using the pixel value thereof. As the number of pixels in 1 cycle of the moire pattern employed in the line deficiency element is obtained from the moire pattern that appeared in the X-ray image, the line deficiency can be accurately corrected even when an X-ray grid having an error or an X-ray grid having a different density is employed.

Further, according to a radiographic apparatus and system of the present invention, it is preferable that the pixel cycle conversion element employs a conversion table. The pixel cycle conversion element can conduct adequately and easily the conversion from a number of the detected peak frequencies to a number of pixels in 1 cycle of the moire pattern by employing the conversion table.

Further, according to a radiographic apparatus of the present invention, it is preferable that; the line deficiency correction element obtains a pixel in the same phase as the line deficiency pixel in the moire pattern by each line from the number of pixels in 1 cycle of the moire pattern obtained by each line orthogonal to the moire pattern line appeared in the X-ray image; and corrects the line deficiency pixel value of each line by using the pixel value in the same phase as the line deficiency pixel obtained by each line. Accordingly, the line deficiency can be accurately corrected by each line.

Further, it is preferable that a radiographic apparatus according to the present invention comprises a pixel extraction element that extracts a preset and predetermined number of pixels among pixels constituting a line orthogonal to a line of a moire pattern appeared in an X-ray image, the Fourier transform element conducts one-dimensional Fourier transform on the pixels extracted by the pixel extraction element. In some cases, the peak frequency indicating the spatial frequency of the moire pattern can be preciously obtained without conducting one-dimensional Fourier transforms on all pixels constituting the lines orthogonal to the lines of the moire pattern in the X-ray image. In such cases, as the number of pixels of lines on which a one-dimensional Fourier transform is conducted can be reduced, a calculation amount to conduct the one-dimensional Fourier transform can be suppressed.

Further, it is preferable that a radiographic apparatus according to the present invention comprises a moire pattern elimination processing element to conduct a processing to eliminate the moire pattern from the X-ray image in which the line deficiency is corrected. The moire pattern elimination processing element can accurately eliminate the moire pattern because the moire pattern is eliminated from the X-ray image in which the line deficiency is accurately corrected by the line deficiency correction element.

Further, according to a radiographic apparatus of the present invention, it is preferable that the moire pattern elimination processing element conducts a processing to eliminate the moire pattern from the X-ray image based on the peak frequency detected by the peak frequency detection element. The peak frequency detected from the results of the one-dimensional Fourier transform is not only employed to correct the line deficiency but also employed to conduct the moire pattern elimination processing by forwarding thereof. As the peak frequency can be employed to conduct both the line deficiency correction and the elimination processing of the moire pattern, the constitution of the apparatus can be simplified and the processing time can be reduced.

Effect of the Invention

According to a radiographic apparatus of the present invention, a Fourier transform element that conducts a one-dimensional Fourier transform on a line orthogonal to a line of a moire pattern appeared in the X-ray image, and a peak frequency detection element that detects a peak frequency indicating a frequency of the moire pattern from the result of the one-dimensional Fourier transform. The detected peak frequency is converted to a number of pixels in 1 cycle of the moire pattern by a pixel cycle conversion element. Then, the line deficiency correction element obtains a pixel of the same phase as the line deficiency pixel in the moire pattern from a number of pixels in 1 cycle of the more patterns, and corrects the line deficiency pixel based by using the pixel value thereof. As the pixel in 1 cycle of the moire patterns employed in correction of the line deficiency is obtained from the more pattern appeared in the X-ray image, the line deficiency can be accurately corrected even if the X-ray gird having an error or the X-ray grid having a different density is employed.

The above, and other aspects, features and advantages of the present invention will become apparent from the follow-

BRIEF DESCRIPTION OF THE DRAWINGS

FIG. 5 is a figure illustrating an example of conversion table.

DETAILED DESCRIPTION OF THE PREFERRED EMBODIMENTS

Figure 1:
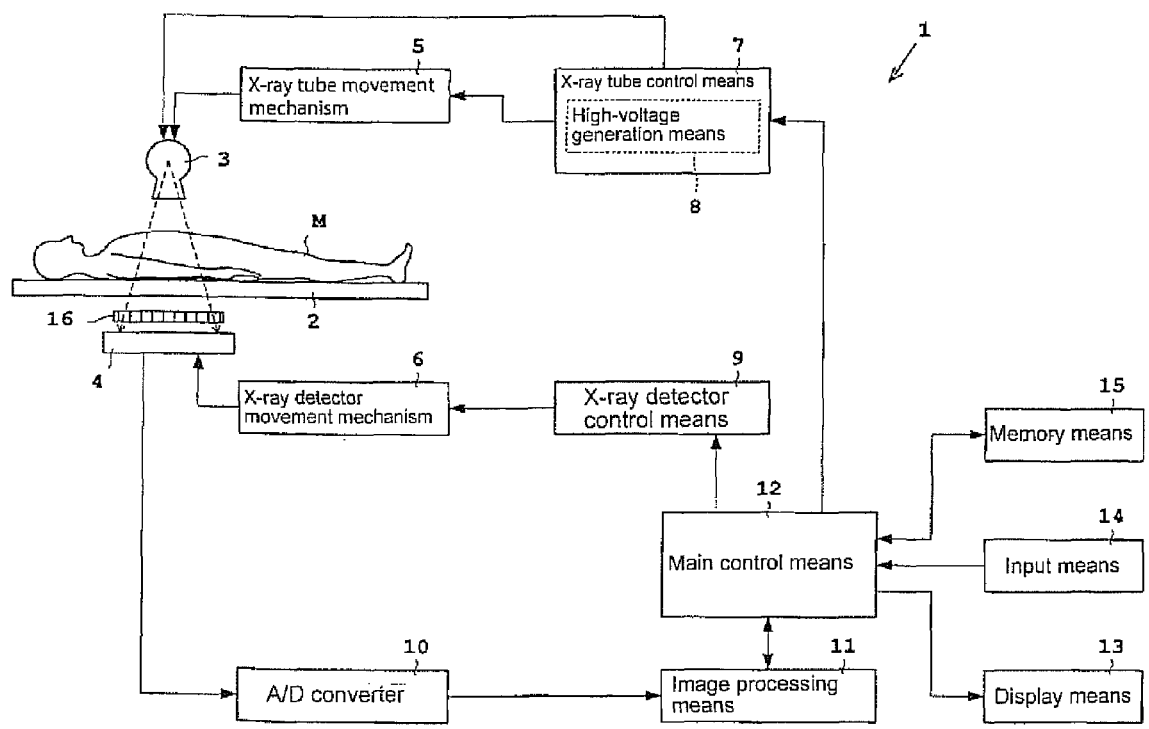
FIG. 1 is a block figure illustrating a constitution of a radiographic apparatus according to Embodiment 1.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale and additional steps or features may be described herein but not shown in the drawings for simplicity. For purposes of convenience and clarity only, directional or time terms, such as top, bottom, up, down, over, above, below, or first, second, last, or then may be used with respect to the drawings. These and similar directional or time terms should not be construed to limit the scope of the invention in any manner. It will be recognized that an apparatus or system so described will be understood to additionally include the description of operative operation of the apparatus or system and supported by a description of the features of the apparatus or system, such that the apparatus, system, and method are mutually operatively enabling and understood by those of skill in the art.

Embodiment 1

Figure 2:
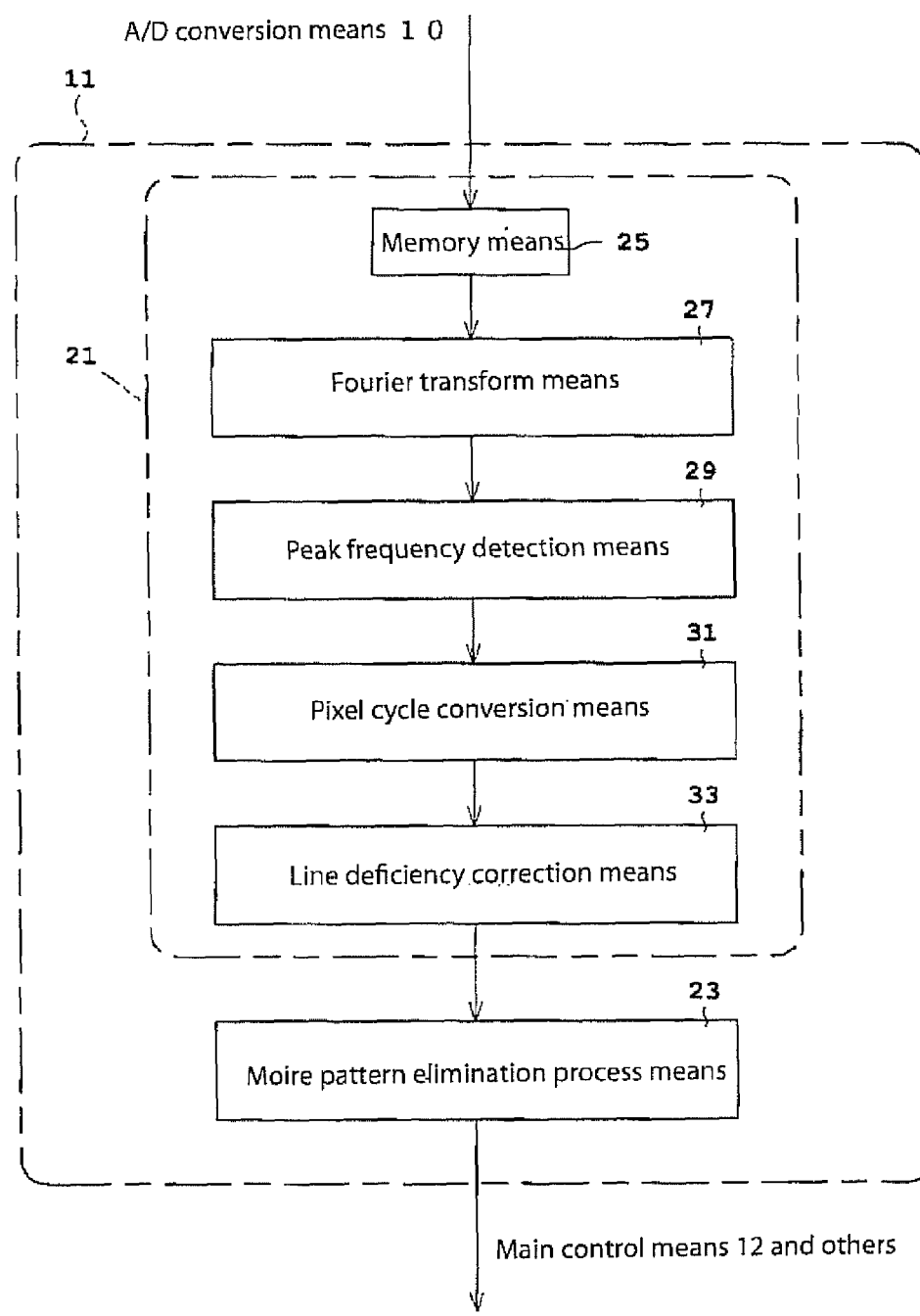
FIG. 2 is a block figure illustrating a constitution of an image processing element of a radiographic apparatus according to Embodiment 1.
Figure 3:
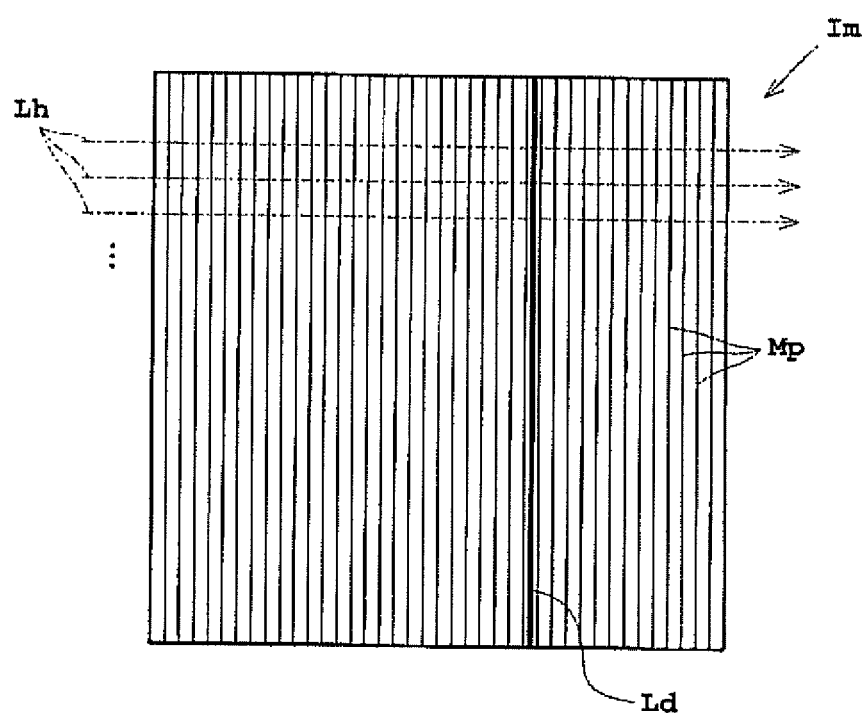
FIG. 3 is a pattern diagram illustrating an example of an X-ray image including a line deficiency and a moire pattern.
Figure 4:
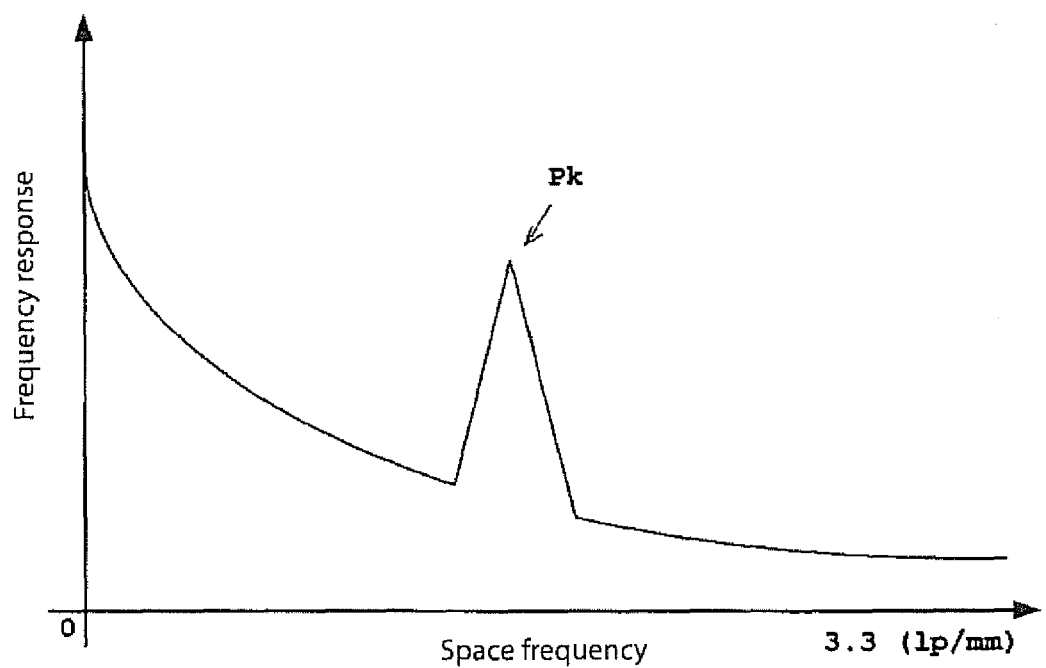
FIG. 4 is a figure illustrating an example of result obtained by Fourier transform.
Figure 6:
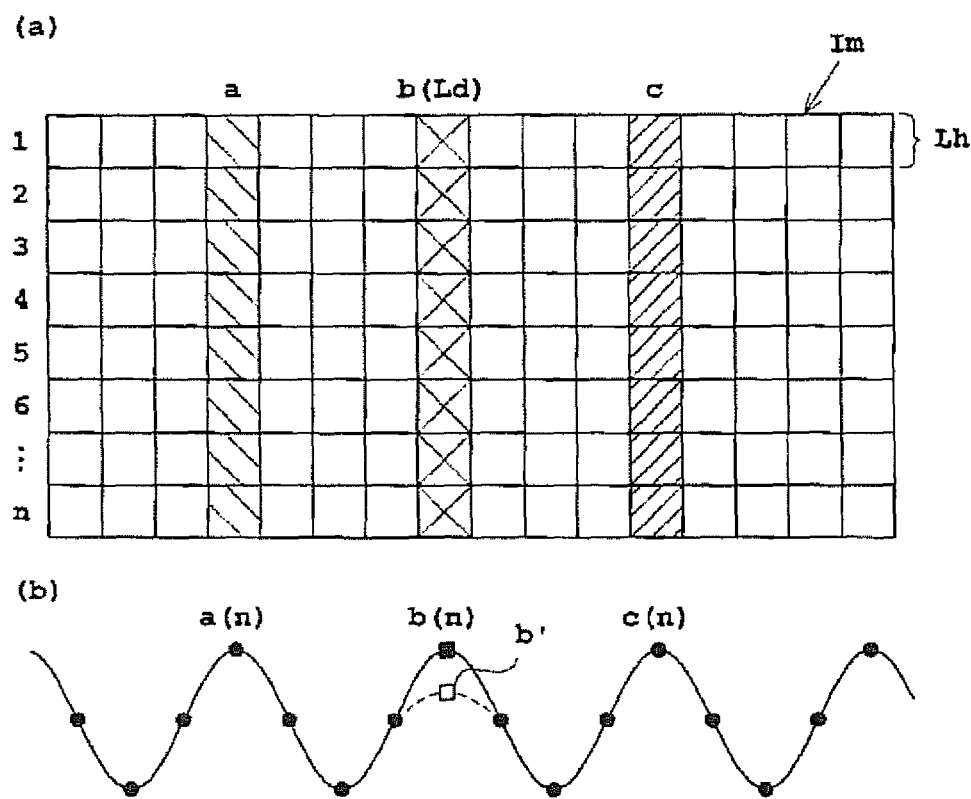
FIG. 6 is illustrating a line deficiency correction, wherein (a) is a line deficiency pixel and a normal pixel employed for correction thereof, and (b) is a wave pattern of a moire pattern.

An exemplary, and non-limiting, Embodiment 1 of the present invention is now illustrated referring to figures. FIG. 1 is a block figure illustrating an exemplary constitution, arrangement, or layout of a radiographic apparatus or system according to Embodiment 1. FIG. 2 is an exemplary block figure illustrating an arrangement and process flow of an image processing element of a radiographic apparatus according to Embodiment 1. FIG. 3 is an exemplary pattern diagram illustrating an example of an X-ray image including a line deficiency and a moire pattern. FIG. 4 is a figure illustrating an example of result obtained by a Fourier transform. FIG. 5 is a figure illustrating an example of conversion table and FIG. 6 is illustrating a line deficiency correction.

Radiographic Apparatus

Referring to FIG. 1, a radiographic apparatus 1 comprises a table 2 on which a subject M is positioned, an X-ray tube 3 that irradiates X-rays to the subject M, and a flat panel X-ray detector 4 (hereinafter FPD) set as facing to X-ray tube 3 detects X-rays passed though the subject M during a use of the proposed invention. In addition, the radiographic apparatus 1 comprises an X-ray tube movement mechanism 5 that operatively moves the X-ray tube 3 and an X-ray detector movement mechanism 6 that operatively moves the FPD 4 during a use or adjustment hereof. Specifically, X-ray tube 3 corresponds to an X-ray irradiation element of the present invention and FPD 4 corresponds to an X-ray detector of the present invention.

An X-ray tube control element 7 having a high-voltage generation element 8 that is operative to generate tube voltage and tube current of the X-ray tube 3 conducts a required control of the X-ray tube 3 that irradiates X-rays in accordance with the operative conditions such as the tube voltage and the tube current that are predetermined by such as an input element 14 as described later. In addition, the X-ray control element 7 conducts any required controls for scanning, e.g. horizontal movement of the X-ray tube 3 and rotation of X-ray tube 3 around the body axis of the subject M, by controlling X-ray tube movement mechanism 5. Further, X-ray control element 7 conducts a setting control of an irradiation area of a collimator (not shown in FIG. 1) that is equipped at the irradiation side of the X-ray tube 3.

An X-ray detector control element 9 conducts any required controls for scanning, e.g. horizontal movement and rotation of FPD 4 around the body axis of the subject M, by controlling X-ray detector movement mechanism 6. Specifically, on a scanning use of the X-ray tube 3 and FPD 4, the X-ray tube and FPD 4 move facing each other so that FPD 4 can detect the X-ray irradiated from the X-ray tube 3. In addition, radiographic apparatus 1 comprises a table movement mechanism that operatively moves a table 2 in a horizontal direction and a vertical direction, and a table control element to control the table movement mechanism (neither is shown in FIG. 1.)

Further, the radiographic apparatus 1 comprises an A/D converter 10 that operatively digitizes and then extracts an X-ray detection signal which is a charge signal from the FPD 4; an image processing element 11 that conducts a variety of processings operations based on the X-ray detection signal output from the A/D converter 10; and a main control element 12 that controls overall each constitution of the radiographic apparatus 1. In addition, the radiographic apparatus 1 comprises a display element 13 comprising, as a non-limiting example, such as a monitor that displays an X-ray image after an image processing, an input element 14 for which an operator employs to conduct operative and various input-setting, and an electronic memory element 15 that operatively stores the X-ray image following the image processing in a memory device.

During an operation, the A/D converter 10 converts the charge signal output from the FPD 4 from analog to digital and outputs a digitized X-ray signal. The main control element 12 comprises such as a central processing unit (CPU) and conducts overall control to run adequately the overall apparatus. An input element 14 comprises such as a mouse and a keyboard. A memory element 15 comprises such as ROM (read-only memory), RAM (random access memory) or a storage medium such as a hard drive.

Further, the radiographic apparatus 1 comprises an X-ray grid 16 set in the side of incident X-ray of the FPD 4 eliminates a scattered radiation through the subject M. The X-ray grid 16 comprises lead and aluminum one after the other in parallel setting.

Image Processing Element

Referring now to FIG. 2, an image processing element 11 comprises a line deficiency correction processing element 21 that corrects a line deficiency occurring in an X-ray image and a moire pattern elimination processing element 23 that conducts elimination processing of a moire pattern due to such as an X-ray grid 16 from the X-ray image of which the line deficiency was corrected by the line deficiency correction processing element 21.

The line deficiency correction processing element 21 comprises a memory element 25, a Fourier transform element 27, a peak frequency detection element 29, a pixel cycle conversion element 31 and a line deficiency correction element 33.

During an operative use, an X-ray detection signal, i.e. an X-ray image, which is output following digital conversion by the A/D converter 10, is once stored in a memory element 25. The X-ray image at this step is shown in FIG. 3. In the X-ray image Im, a line deficiency Ld occurs in the vertical direction of the X-ray image Im thereof and a moire pattern Mp due to such as the X-ray grid 16, wherein the lines ascribe to appearing as arraying in a near-vertical direction of the X-ray image Im.

Referring to FIG. 3, the Fourier transform element 27 conducts a one-dimensional Fourier transform on each line Lh near-orthogonal to lines of the moire pattern Mp appeared in the X-ray image Im. Specifically, the one-dimensional Fourier transform by each line Lh that is a pixel array in a horizontal direction of the X-ray image. The one-dimensional Fourier transform is conducted by e.g. a fast Fourier transform (FFT). In addition, the one-dimensional Fourier transform is conducted 1 line by 1 line in order from e.g. the upper end of the X-ray image Im. When the one-dimensional Fourier transform is conducted on 1 line, the result of one-dimensional Fourier transform is forwarded to the peak frequency detection element 29 (as well as the peak frequency detection element 29, the pixel cycle conversion element 31 and the line deficiency correction element 33 and so forth) by a line.

The peak frequency detection element 29 detects the peak frequency from the result of one-dimensional Fourier transform. Referring further now to FIG. 4, there is unnaturally prominent portion in a wave pattern of result of one-dimensional Fourier transform. The space frequency [lp/mm] that provides the maximum frequency response of this portion is detected as the peak frequency Pk. The peak frequency Pk indicates the space frequency of the moire pattern Mp.

Further, the peak frequency detection element 29 may detect the peak frequency Pk in the preset range of space frequency based on results of one-dimensional Fourier transform. When the X-ray grid 16 having the density of 5 [lp/mm] (error±10%) is employed, for example, the peak frequency Pk in the range of 1.25 [lp/mm]-2.24 [lp/mm] may be detected.

During operation, the pixel cycle conversion element 31 converts the peak frequency Pk detected by the peak frequency detection element 29 to a number of pixels in 1 cycle of the moire pattern Mp. Specifically, it converts the peak frequency Pk indicating the space frequency of the moire pattern Mp to the number of pixels of 1 cycle of the wave pattern of peak frequency (how many pixels in 1 cycle), in other word to a format indicating how many pixels are included in 1 cycle. Further, 1 cycle of the moire pattern is 1 [lp]. The pixel frequency conversion element 31 employs a conversion table 35 as shown in FIG. 5. For example, when the peak frequency Pk is 1.6 [lp/mm], the conversion provides 1 cycle by 4 pixels, when it is 1.9 [lp/mm], the conversion provides 1 cycle by 7 pixels (3.5 pixels×2).

Referring to FIG. 5, a conversion table 35 is preset so that the peak frequency Pk detected by the peak frequency detection element 29 corresponds to a number of pixels in 1 cycle of the moire pattern Mp. Firstly, when a radiography is taken by using the FPD 4 having the resolution of 3.3 [lp/mm] and the pattern of 3.3 [lp/mm] appears in an X-ray image, the pattern appears as 1 cycle by 2 pixels in the relationship. Accordingly, when the moire pattern Mp having the predetermined peak frequency Pk [lp/mm] appears in the X-ray image, the number of pixels Px in 1 cycle of the moire pattern can be expressed as the ratio obtained by Formula (1), below. Further, Formula (1) can be expressed as Formula 2, below. Accordingly, the number of pixels Px in 1 cycle of the moire pattern can be obtained from the peak frequency Pk.

$$3.3 \text{ [lp/mm]}/(\tfrac{1}{2}[\text{pixel}])=Pk \text{ [lp/mm]}/(1/Px[\text{pixel}]) \quad (1)$$

$$Px[\text{pixel}]=(3.3 \text{ [lp/mm]}/Pk \text{ [lp/mm]})\times 2 \text{ [pixel]} \quad (2)$$

Further, in many cases, the number of pixels obtained from Formulae (1) and (2) may include a numeric number after decimal point. Therefore, the number of pixels should be adjusted to become a positive integer. For example, the number after decimal point of the number of pixels Px can be either rounded up or truncated. According to a non-limiting illustrative Embodiment of the present invention, for example, if the number is not bigger than 4.25 and not smaller than 3.75, it is set as 4 pixels. Further, if it is not smaller than 3.25 and not bigger than 3.75, it is set as 3.5 pixels in between 3 pixels and 4 pixels. In this scenario, 7 pixels multiplied 3.5 by 2 are provided as the number of pixels Px in 1 cycle of the moire pattern Mp. Referring to FIG. 5, when the peak frequency Pk [lp/mm] is 1.4, 1.5, 1.8 or 1.9, 9 pixels multiplied 4.5 by 2 or 7 pixels multiplied 3.5 by 2 are set as the number of pixels Px in 1 cycle of the moire pattern Mp.

Specifically, the adjustment to obtain a positive integer for a number of pixels Px is set as the number of pixels Px in 1 cycle of the moire pattern Mp after obtaining the positive integer number of pixels Px corresponding to the (positive integral) cycle of the moire pattern Mp. According to Embodiment of the present invention, it is replaced to the number of pixels having 0.5 pixel intervals and the number of pixels including a number after decimal point is multiplied by 2. Thereby, the more accurate cycle of the moire pattern Mp can be expressed as the positive integer number of pixels.

During an operative use, the line deficiency correction element 33 obtains a pixel of the same phase as the line deficiency of 1 cycle of the moire pattern from a number of pixels of 1 cycle of the moire pattern Mp converted by the pixel cycle conversion element 31 and then corrects the line deficiency pixel by using the pixel value thereof. Referring to FIG. 6 (a), it is deemed that the line deficiency b (Lb) in a vertical direction occurs in the X-ray image Im and the moire pattern Mp having the lines in near vertical direction appears as 1 cycle by 4 pixels. When the line deficiency correction element 33 corrects the line deficiency pixel b1 of the first line, it obtains a value of the pixel of the same phase as the line deficiency pixel b1 in the moire pattern Mp, i.e. the value of the adjacent pixel a1, c1 by 4 pixels for the line deficiency pixel b1 in right-and-left sides in a horizontal direction (distant 4 pixels in both side). Then the line deficiency correction element 33 corrects the line deficiency pixel b1 by using the average value of the values of pixel a1, c1 as a value of the line deficiency pixel b1. The same processing is conducted after the second line and given b(n) is the line deficiency pixel and a(n) or c(n) is the normal pixel of the same phase, the pixel value correcting the line deficiency pixel b(n) can be obtained according to the following formula (3).

$$b1=(a1+c1)/2, b2=(a2+c2)/2, \ldots, b(n)=[a(n)+c(n)]/2 \quad (3)$$

Further, referring to FIG. 6(b), when the cycle of the moire pattern Mp has 1 cycle by 4 pixels, the pixel of the same phase as the line deficiency pixel b(n) in the moire pattern Mp is the normal pixel a(n), c(n) adjacent by 4 pixels in right-and-left sides in a horizontal direction. If the normal pixels a(n), c(n) of the same phase as the line deficiency pixel in the moire pattern are employed to correct the line deficiency pixel b(n), the correction can be conducted without disturbing the wave patter of the moire pattern. However, if the correction is conducted by using a normal pixel of the different phase, for example, as indicated as the sign b', the correction would be conducted under disturbed condition of the wave pattern of the moire pattern.

In addition, the position of the line deficiency pixel b(n) in the X-ray image Im can be optionally designated by operator's input on the line deficiency Ld corrected by the line deficiency correction element 33; or, for example, the position of the line deficiency pixel can be designated by automatic judgment of the pixel showing an abnormal value compared to other pixels.

A moire pattern elimination processing element 23 conducts processing to eliminate a moire pattern Mp from an X-ray image Im of which a line deficiency Id is corrected. For a non-limiting example, a low-pass filter processing is conducted on each line Lh in a direction near orthogonal to a line of the moire pattern Mp. Or after conducting a high-pass filter processing on each line Lh in a direction near orthogonal to a line of the moire pattern Mp and extracting the moire pattern Mp of each line Lh, a differentiation of the moire pattern of each line Lh extracted from the X-ray image Im in which the moire pattern appears is conducted. According to these processing, only a moire pattern component can be eliminated from the X-ray image Im. Meanwhile the moire pattern elimination processing element 23 can employ any known method as far as the method conducts a processing that eliminates the moire pattern Mp.

In addition, after the moire pattern is eliminated from the X-ray image Im, an image processing element 11 conducts any other necessary processing on the X-ray image Im.

Operation of Radiographic Apparatus

Figure 7:
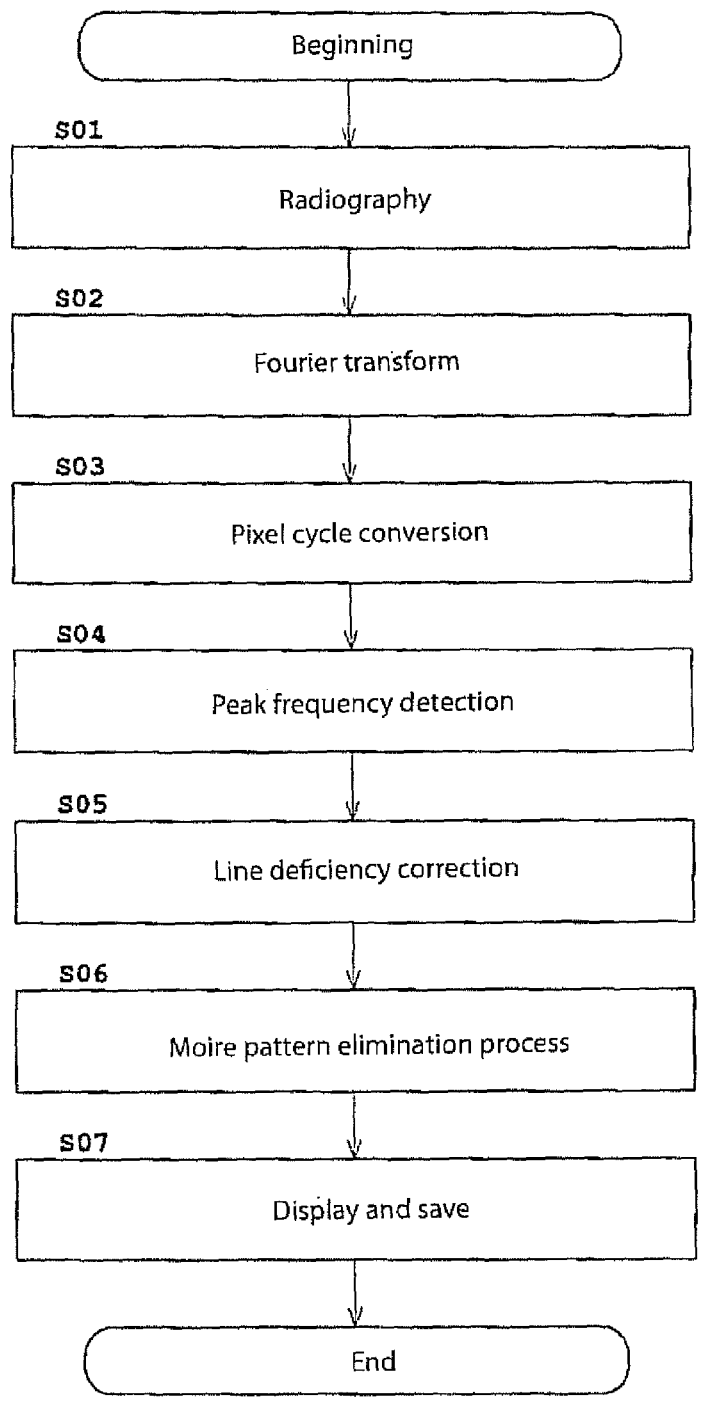
FIG. 7 is a flowchart figure illustrating an operational method of a radiographic apparatus.

Next, an exemplary and optional operation of a radiographic apparatus 1 is illustrated according to the flowchart of FIG. 7.

STEP S01 Radiography: X-rays are irradiated from an X-ray tube 3 to a subject M on a table 2. X-rays irradiated from the X-ray tube 3 pass through the subject M and an incident X-ray to a FPD 4 via an X-ray gird 16 is detected by the FPD 4. A scattered radiation scattered in the subject M is eliminated by the X-ray grid 16 at this time. The FPD 4 outputs an X-ray detection signal corresponding to an intensity distribution of X-ray and the X-ray detection signal output from the FPD 4 is converted to a digital signal by an A/D converter 10. The X-ray detection signal converted to the digital signal, i.e. an X-ray image, is forwarded to an image processing element 11 and is stored once in a memory element 25 of a line deficiency correction processing element 21. Referring to FIG. 3, it is deemed that a line deficiency Ld in a vertical direction of the X-ray image Im thereof occurs in the X-ray image obtained in this manner and a moire pattern Mp in which the lines are in near vertical direction appears.

STEP S02 Fourier Transform: A Fourier transform element 27 conducts a one-dimensional Fourier transform on each line in near orthogonal direction to the lines of the moire pattern appeared in the X-ray image, for example, 1 line by 1 line in order from the upper end of the X-ray image. When the one-dimensional Fourier transform is conducted as shown in FIG. 4, the wave pattern having an unnatural prominent part (frequency characteristic) is obtained.

STEP S03 Peak frequency detection: A peak frequency detection element 29 detects a peak frequency Pk based on the result of one-dimensional Fourier transform. Specifically, referring to FIG. 4, there is an unnaturally prominent part in the wave pattern (frequency characteristic) as the result of Fourier transform and a space frequency [lp/mm] at the point where the frequency response becomes maximal is obtained. The space frequency [lp/mm] at this point is the peak frequency Pk. The peak frequency Pk indicates the space frequency [lp/mm] of the moire pattern. The peak frequency detection element 29 detects the peak frequency Pk at each line based on the result of one-dimensional Fourier transform conducted on each line of the X-ray image.

STEP S04 Pixel cycle conversion: Referring to FIG. 5, and during operation, a pixel cycle conversion element 31 converts the peak frequency Pk detected by the peak frequency detection element 29 to a pixel number of pixels Px in 1 cycle of the moire pattern Mp (e.g. 1 cycle by 4 pixels) by employing a conversion table 35. Referring to FIG. 5, if the peak frequency Pk is 1.6 [lp/mm], it is converted to 1 cycle by 4 pixels and if the peak frequency is 1.9 [lp/mm], is converted to 1 cycle by 7 pixels. The pixel cycle conversion element 31 converts the peak frequency Pk detected at each line of the X-ray image to a number of pixels in 1 cycle of the moire pattern on each line.

STEP S05 Line deficiency correction: The line deficiency correction element 33 obtains a pixel of the same phase as the line deficiency pixel in 1 cycle of the moire pattern from a number of pixels Px in 1 cycle of the moire pattern Mp and corrects the line deficiency pixel by using the pixel value. Referring to FIG. 6, for example, in the case of a moire pattern having 1 cycle by 4 pixels, an average value of adjacent pixel values by 4 pixels from the line deficiency pixel in right-and-left sides in a horizontal direction is obtained and the average value is employed as the pixel value of the line deficiency pixel for correction. In the case of a moire pattern having 1 cycle by 7 pixels, an average value of adjacent pixel values by 7 pixels from the line deficiency pixel in right-and-left sides in a horizontal direction is obtained and the average value is employed as the pixel value of the line deficiency pixel for correction. The line deficiency correction element 33 obtains a pixel of the same phase as the line deficiency positioned on each line of the moire pattern on each line from a number of pixels in 1 cycle, which is converted at each line of the X-ray image, and corrects the line deficiency pixel on each line by using the pixel value of the same phase as the line deficiency pixel that is obtained at each line.

STEP S06 Moire pattern elimination processing: A moire pattern is eliminated by a moire pattern elimination processing element 23 from the X-ray image of which the line deficiency is corrected. As the line deficiency is accurately corrected without disturbing the wave pattern of the moire pattern MP of the line deficiency part by the line deficiency correction element 33, the moire pattern elimination processing element 23 can eliminate accurately the moire pattern Mp.

STEP S07 Display and Save: An image processing element 11 conducts any other necessary processing on the X-ray image Im of which a moire pattern is eliminated. The X-ray image Im of which an image processing is conducted is displayed on a display element 13 and saved in a memory element 15.

According to a further exemplary radiographic apparatus of Embodiment 1, a Fourier transform element 27 conducts a one-dimensional Fourier transform of each line Lb near-orthogonal to lines of a moire pattern Mp appeared in an X-ray image Im, and the peak frequency detection element 29 detects the space frequency providing the maximum frequency response of the unnaturally prominent portion from results of the one-dimensional Fourier transform as a peak frequency Pk. The detected peak frequency Pk is converted to a number of pixels Px in 1 cycle of the moire pattern Mp by the pixel cycle conversion element 31. And then, the line deficiency correction element 33 obtains a pixel of the same phase as the line deficiency pixel in 1 cycle of the moire pattern from a number of pixels Px in 1 cycle of the moire pattern Mp (e.g. a pixel value of adjacent pixels by 4 pixels from the line deficiency pixel in right-and-left sides in a horizontal direction) and corrects the line deficiency pixel by using the pixel values (e.g. the average value thereof as the line deficiency pixel). Since the number of pixels Px in 1 cycle of the moire pattern MP employed with the line deficiency correction element 33 is directly obtained from the moire pattern appeared in the obtained X-ray image Im, the line deficiency can be accurately corrected even if an X-ray grid having an error or an X-ray gird having a different density is employed.

Figure 8:
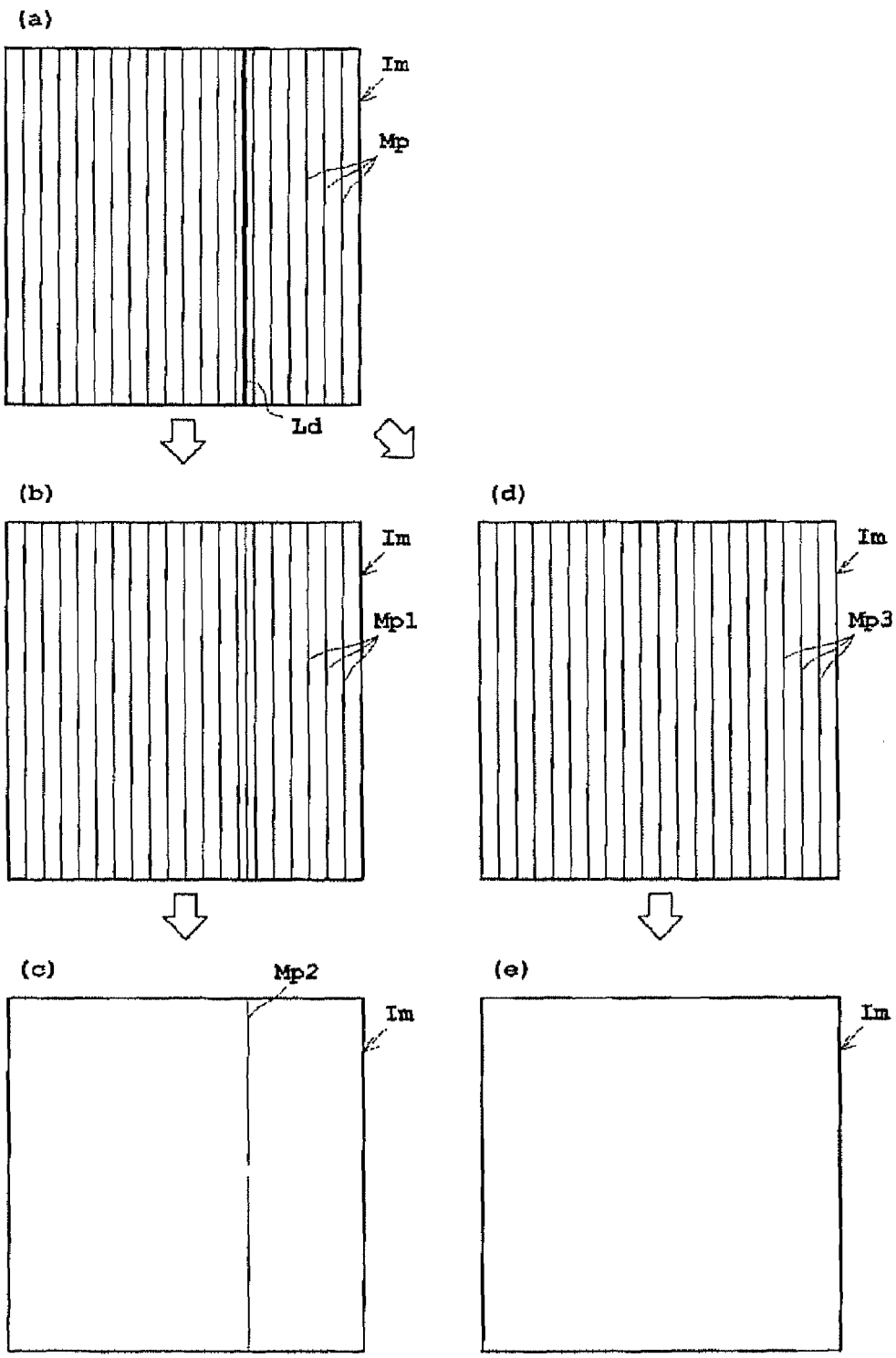
FIG. 8 is a figure illustrating an effect of a radiographic apparatus and system, wherein (a) is an original X-ray image, (b) is an example when a line deficiency correction is conducted by employing a conventional apparatus, (c) is an example when a moire pattern elimination processing is conducted following the line deficiency correction conducted by a conventional apparatus, (d) is an example when a line deficiency correction is conducted in accordance with the present invention, and (e) is an example when a moire pattern elimination processing is conducted following the line deficiency correction in accordance with the present invention.

In addition, since the line deficiency can be accurately corrected, a processing step to eliminate the moire pattern can be accurately conducted thereafter. For example, referring to FIG. 8, a line deficiency Ld in a vertical direction in the X-ray image Im occurs, and also a moire pattern in which the lines array along near vertical direction appears. According to a conventional apparatus, if correction of a line deficiency Ld cannot be accurately conducted, the wave pattern of the corrected line deficiency Ld in the moire pattern Mp1 remains disturbed as shown in FIG. 8(b). If a moire pattern elimination processing is conducted under such condition, a moire pattern Mp2 remains in the part of the corrected line deficiency Ld as shown in FIG. 8(c). In contrast, according to a radiographic apparatus 1 of the present proposed optional Embodiment, the line deficiency Ld can be accurately corrected as shown in FIG. 8(d); and therefore after the moire pattern elimination processing, the part of the line deficiency Ld can be accurately eliminated as shown FIG. 8(e) following the correction of moire pattern Mp3.

In addition, the pixel cycle conversion element 31 can easily and adequately convert the conversion from a detected peak frequency to a number of pixels in 1 cycle by employing the conversion table 35.

In addition, the line deficiency correction element 33 obtains a pixel of the same phase as the line deficiency pixel in the moire pattern Mp on each line Lh from a number of pixels Px in 1 cycle of the moire pattern Mp obtained at each line Lh near orthogonal to the lines of the moire pattern Mp appeared in the X-ray image Im, and corrects the line deficiency pixel value of each line Lh by using the pixel value of the same phase as the line deficiency pixel obtained on each line Lh so that the line deficiency Ld can be accurately corrected at each line.

Embodiment 2

Figure 9:
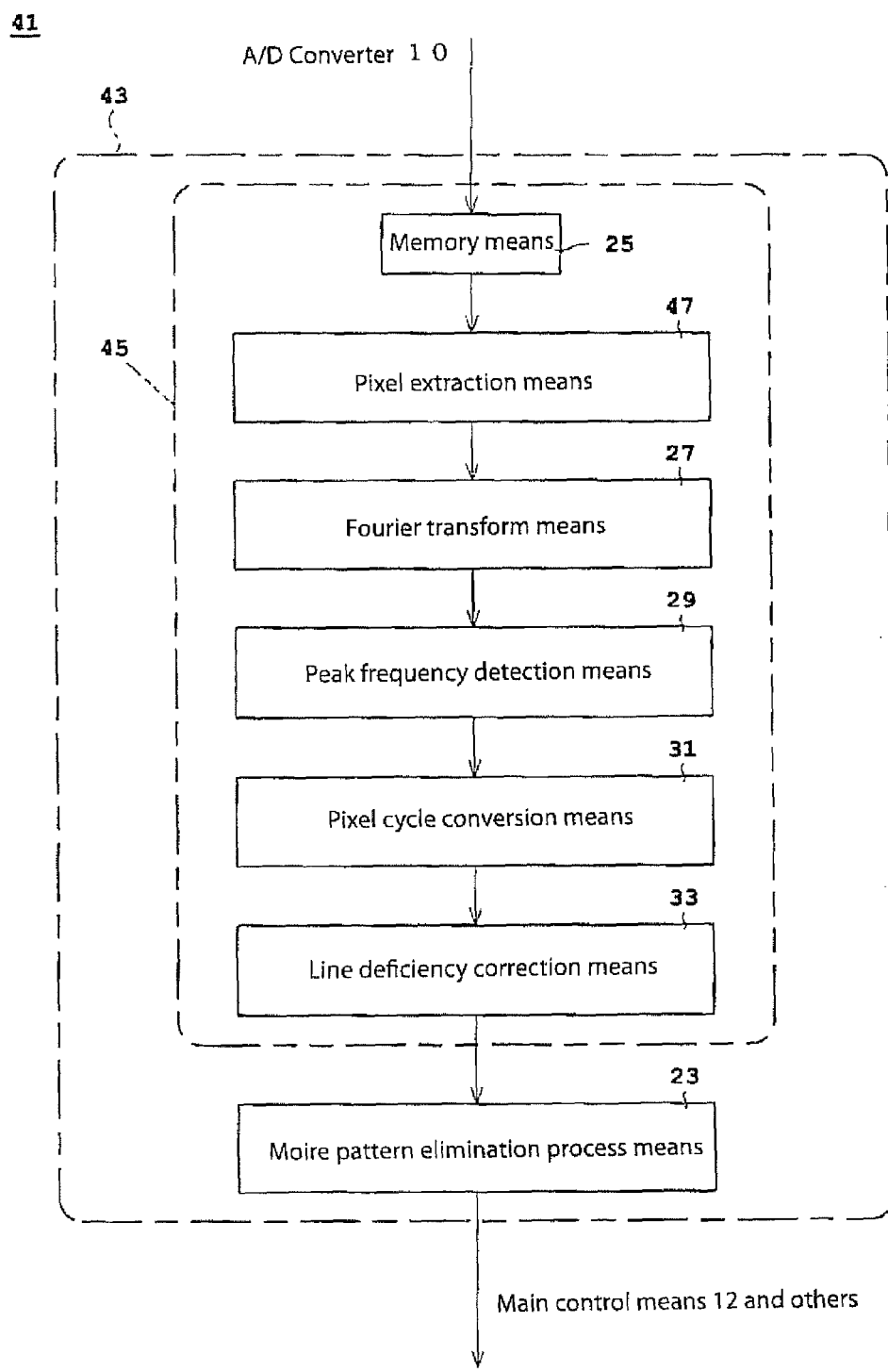
FIG. 9 is a block figure illustrating a constitution of an image processing element of a radiographic apparatus according to Embodiment 2.

Next, an exemplary, and non-limiting, Embodiment 2 of the present invention is illustrated referring to FIG. 9 which is a block figure illustrating an exemplary constitution or arrangement of an image processing element according to Embodiment 2. Further, the illustration of redundant constitution as in Embodiment 1 is not described but is incorporated herein by reference.

According to Embodiment 1, a one-dimensional Fourier transform on a line Lh in near orthogonal direction of the lines of a moire pattern Mp appeared in a X-ray image, i.e. each line Lb in a horizontal direction of the X-ray image Im, is conducted on all pixels constituting 1 line, for example, one 1 line by 1 line in order from the upper end. However, it is not limited to this manner. Specifically, a Fourier transform may be conducted on extracted pixels following an extraction of preset and predetermined number of pixels from pixels constituting 1 line.

Specifically, referring to FIG. 9, a line deficiency correction element 45 of an image processing element 43 of an radiographic apparatus 41 has a pixel extraction element 47, which extracts preset and predetermined number of pixels from pixels constituting lines Lh in near orthogonal direction of lines of a moire pattern Mp, in front of a Fourier transform element 27. A number of pixels required to accurately correct by a line deficiency correction element 33 is preset in the pixel extraction element 47. The Fourier transform element 27 conducts a one-dimensional Fourier transform on extracted pixels by the pixel extraction element 43. In addition, when Fourier transform is conducted by a fast Fourier transform (FFT), it is preferable that the extracted pixels are a number of power-of-2.

According to Embodiment 2, in a radiographic apparatus 41, a pixel extraction element 47 extracts preset and predetermined number of pixels from pixels constituting lines Lb near orthogonal to lines of a moire pattern Mp, and a Fourier transform element 27 conducts a one-dimensional Fourier transform on the extracted pixels. In some cases, a peak frequency Pk indicating a space frequency of a moire pattern Mp can be preciously obtained without conducting the one-dimensional Fourier transform on all of pixels constituting lines Lh which are near orthogonal to the lines of the moire pattern Mp in the X-ray image Im. In such cases, since the number of pixels constituting lines Lh can be reduced, a calculation amount of Fourier transform can be suppressed. In addition, if the extracted pixels are in power-of-2, the fast Fourier transform (FFT) can be effectively conducted.

Embodiment 3

Figure 10:
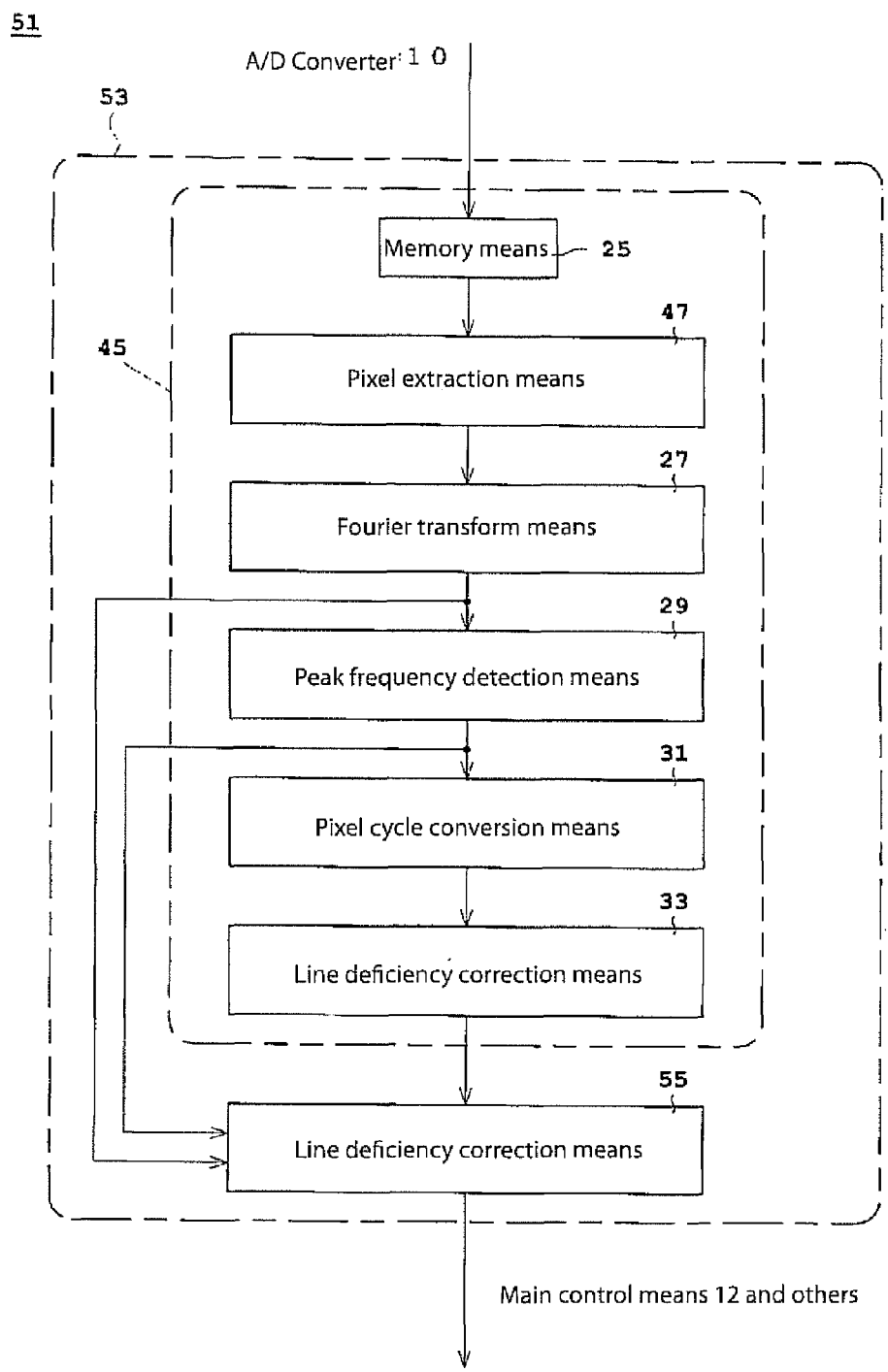
FIG. 10 is a block figure illustrating a constitution of an image processing element of a radiographic apparatus according to Embodiment 3.
Figure 11:
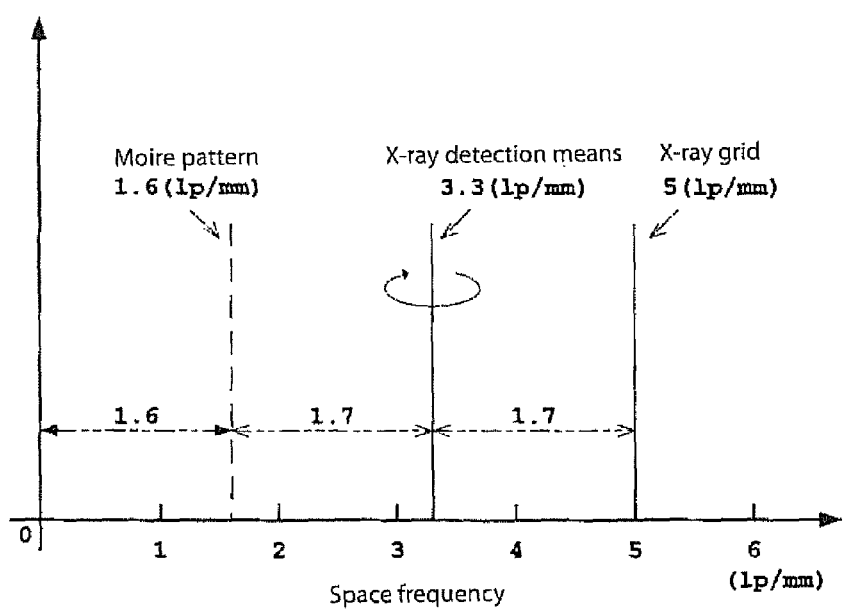
FIG. 11 is a figure illustrating a method to calculate a space frequency of a moire pattern appeared in an X-ray image by a resolution of an X-ray detector and a density of an X-ray grid.
Figure 12:
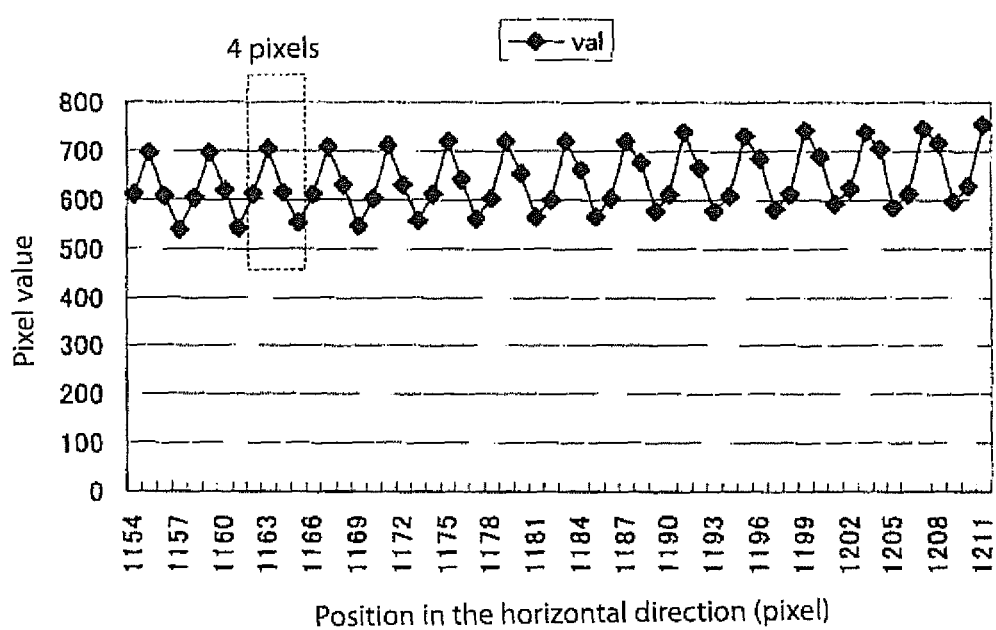
FIG. 12 is a figure illustrating a number of pixels in 1 cycle of a more pattern when an X-ray grid is 5 [lp/mm].
Figure 13:
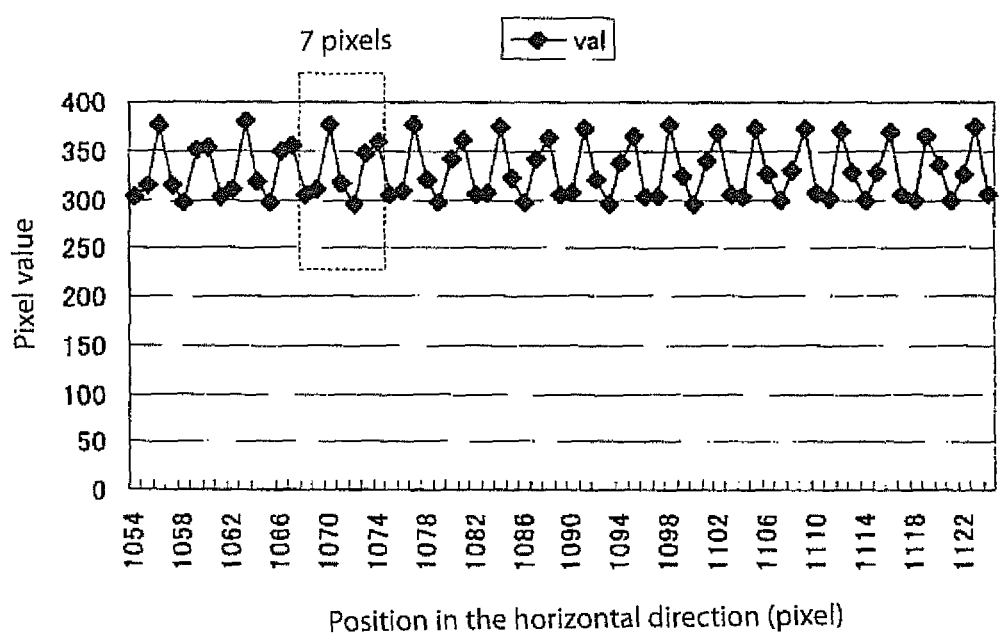
FIG. 13 is a figure illustrating a number of pixels in 1 cycle of a moire pattern when an X-ray grid is 4.7 [lp/mm] with an error instead of 5 [lp/mm].

Next, an exemplary and non-limiting Embodiment 3 of the present invention is illustrated referring to FIG. 10 as a block figure illustrating a constitution of an image processing element of according to Embodiment 3. Further, the illustration of redundant constitution as in Embodiment 1 or 2 is not described, but the contents thereof are again incorporated by reference.

According to Embodiment 1 or Embodiment 2 as described above, a line deficiency 21, 45 comprises a Fourier transform element 27 and a peak frequency detection element 29, or a pixel extraction element 47, a Fourier transform element 27 and a peak frequency detection element 29, and conducts processing to correct a line deficiency Ld. In contrast, if a moire pattern elimination processing element 23 comprising a Fourier transform element and a peak frequency detection element, or a pixel extraction element, a Fourier transform element and a peak frequency detection element conducts a processing to eliminate a moire pattern, the moire pattern elimination processing element 23 conducts repeatedly the same processing as the line deficiency correction processing element 21, 45.

Then, referring to FIG. 10, in an exemplary image processing element 53 of a radiographic apparatus 51, a moire pattern elimination processing element 55 conducts a processing to eliminate a moire pattern Mp from a X-ray image Im based on the peak frequency Pk detected by a peak frequency detection element 29 of a line deficiency correction processing element 45. The moire pattern elimination processing element 55, for example, obtains first a coefficient of a FIR filter to extract the moire pattern Mp on each line Lh based on the peak frequency Pk detected on each line Lh of the X-ray image Im, and then extracts the moire pattern image by conducting a FTR filter on each line Lg of the X-ray image by using the obtained coefficient. Then, it conducts to eliminate the moire pattern from the X-ray image by differentiating the moire pattern image from the X-ray image Im.

In addition, referring to FIG. 10, when the pixel extraction element 47 is not employed, the moire pattern elimination processing element 55 may optionally conduct processing to eliminate the moire pattern Mp from the X-ray image Im, based on the result of one-dimensional Fourier transform conducted by the Fourier transform element 27 of the line deficiency correction processing element 45 and the peak frequency pk detected by the peak frequency detection element 29. For example, a filter (mask) on each line Lh first is generated based on the peak frequency Pk conducted for each line Lh of the X-ray image Im to eliminate the moire pattern from the result of one-dimensional Fourier transform, and the moire pattern elements is eliminated by a filer processing from the result of each line Lb for which one-dimensional Fourier transform is conducted by using the generated filer of each line Lh. And further the moire pattern Mp is eliminated from the x-ray image Im by conducting a one-dimensional inverse Fourier transform on the result of each filter processed line Lh.

Further regarding radiographic apparatus 51, according to Embodiment 3, the result of a one-dimensional Fourier transform by the Fourier transform element 27 and the peak frequency Pk detected by the peak frequency detection element 29 in the line deficiency correction element 45 are not employed only to correct line deficiency but also are employed following forwarding to moire pattern elimination processing element 55. Specifically, since a part of the line deficiency correction processing element 45 and a part of the moire pattern elimination processing element 55 can be operatively shared, the constitution or arrangement of radiographic apparatus 51 can be simplified and also the processing time thereby can be reduced.

It will be understood by those of skill in the art, that the present invention is not limited to the above exemplary embodiments, and can be applied to the following further Embodiments.

(1) According to the above Embodiment 1 or 2, a one-dimensional Fourier transform is first conducted on each line Lh near orthogonal to lines of a moire pattern Mp appeared in an X-ray image Lm. Next, a peak frequency Pk is detected from the result of one-dimensional Fourier transform on each line Lh and the detected peak frequency Pk is converted to a number of pixels Px in 1 cycle of the moire pattern Mp. And then the line deficiency pixels constituting a line deficiency Ld in each line Lh is corrected. However, the embodiment is not limited to this manner and may be adapted within the scope of the present invention. For example, a number of pixels Px in 1 cycle of a moire pattern Mp appeared an X-ray image Im that is taken for setting or a standard number of pixels Px in 1 cycle of a moire pattern Mp based on predetermined number of lines Lh are obtained and set before taking X-ray image Im, and then the line deficiency Ld can be corrected by using the number of pixels in 1 cycle of the preset moire pattern Mp corresponding to the X-ray image taken later.

(2) Further, according to above each Embodiment, and those Embodiments herein, an average value of normal pixels of 1 cycle (e.g. 4 pixels) in right-and-left sides in a horizontal direction corresponding to the line deficiency pixel is obtained and the line deficiency pixel is corrected, but it is optionally not limited to such a manner. For example, an average value of normal pixels of 2 cycles in right-and-left sides in a horizontal direction corresponding to the line deficiency pixel is obtained and the line deficiency pixel can be corrected. In addition, an average value of normal pixels of 1 adjacent cycle in right-and-left sides in a horizontal direction in which the line deficiency pixel is positioned is obtained, and then the line deficiency is corrected; but it is not limited to this manner. For a non-limiting example, referring to FIG. 6($a$), when the line deficiency pixel 5 is corrected, an average value of plural pixels including normal a5 and c5 in 1 adjacent cycle, and further top-and-bottom normal pixels thereof (a4, a6, b4 and b6) are obtained, and then the line deficiency pixel b5 may be corrected. Specifically, according to b5=(a4+a5+a6+b4+b5+b6)/6, the line deficiency pixel b5 is corrected.

(3) According to above each Embodiment, and the other adaptive embodiments discussed herein, referring to FIG. 5, the pixel cycle conversion element 31 optionally converts the detected peak frequency Pk to a number of pixels in 1 cycle of the moire pattern Mp by employing the conversion table 35, but it is not limited to this manner. Specifically, the detected line deficiency Pk is substituted into the above formula (2) to calculate the number of pixels Px1 in 1 cycle of the moire pattern Mp, and then the calculated number of pixels Px1 may be converted to the positive integer number of pixels Px2. For example, when the number of pixels, not smaller than 3.75 and not bigger than 4.25, is converted to 4 pixels by employing the conversion table; and if the calculated number of pixels Px1 is 4.125 pixels (wherein the peak frequency Pk is 1.6 [lp/mm]); it is converted to 4 pixels.

(4) According to above each Embodiment, and the other adaptive embodiments discussed herein, after the image processing elements 11, 43, 55 completes the line processing of 1 line of the X-ray image, they are forwarded to the next constituent by a line; but this is not limited to this manner. Specifically, after the processing of all lines is completed, they can be forwarded to the next constitution by an X-ray image, as a further exemplary embodiment.

(5) According to above each Embodiment, and the other adaptive embodiments discussed herein, a radiographic apparatus 1, 41, 51 comprise a flat panel X-ray detector (FPD) as an X-ray detector, but it is not limited to this constitution. Specifically, it may also comprise an image intensifier.

EXPLANATION OF REFERENCES 1, 41, 51: Radiographic apparatus
3: X-ray tube

4: Flat panel X-ray detector (FPD)
11, 43, 53: Image processing element
16: X-ray grid
21, 45: Line deficiency correction processing element
23, 55: Moire pattern elimination processing element
27: Fourier transform element
29: Peak frequency detection element
31: Pixel cycle conversion element
33: Line deficiency correction element
35: Conversion table
47: Pixel extraction element
Lh: Line in a orthogonal direction to a line of moire pattern
Ld: Line deficiency
Mp: Moire pattern
Pk: Peak frequency
Px: Number of pixels in 1 cycle of a moire pattern It will be understood by those of skill in the art that the use of the phrase constitute, constitution, exemplary, embodiment, illustration, step, or system are provided as assistive aids to the reader and are not used to imply a required limiting arrangement or structure or assembly of features or aspects or method steps to the invention. The aspects of the invention as discussed herein are to be considered broadly and without limitation. For example, the above method steps may be modified for use during operation of the apparatus and systems proposed, such that multiple methods of operating a radiographic apparatus or correcting an image or a line deficiency may be readily accommodated without departing from the scope of the proposed invention. It will be further understood by those of skill in the art that the use of the phrase means may be interchangeably used with the phrase element to be understood by those of suitable skill. Thus, that the feature, aspect, means, or element will be as described and function as described.

Having described at least one of the preferred embodiments of the present invention with reference to the accompanying drawings, it will be apparent to those skills that the invention is not limited to those precise embodiments, and that various modifications and variations can be made in the presently disclosed method and system for preheating of semiconductor material for laser annealing and gas immersion laser doping without departing from the scope or spirit of the invention. Thus, it is intended that the present disclosure cover the modifications and variations of this disclosure provided they come within the scope of the appended claims and their equivalents. It is further intended that phrases apparatus and system are non-limiting, such that any apparatus may be understood as a system and thus a system may be understood as an apparatus without specific limitation to any particular shape, assembly, or location of elements.

What is claimed is:

1. A radiographic apparatus, comprising:
    a radiation element that irradiates X-rays to an external subject;
    an X-ray detector that detects said X-rays passed through the subject; and
    an X-ray grid that is set in an X-ray incident side of said X-ray detector and eliminates scattered lines,
    wherein said radiographic apparatus is operative to obtain an X-ray image during a use based on said X-rays detected by said X-ray detector, and wherein radiographic apparatus further comprises:
        a Fourier transform element that conducts a one-dimensional Fourier transform on a line orthogonal to a line of a moire pattern appearing in said X-ray image, said one-dimensional Fourier transform having a result;
        a peak frequency detection element that detects a peak frequency from the result of said one-dimensional Fourier transform;
        a pixel cycle conversion element that converts said peak frequency to a number of pixels in one (1) cycle of a moire pattern; and
        a line deficiency correction element that obtains pixels of the same phase as line deficiency pixels in the moire pattern from the number of pixels in one (1) cycle of said moire pattern, and corrects said line deficiency pixel by using the pixel value of the obtained pixels.

2. A radiographic apparatus, according to claim 1, further comprising:
    a conversion table in said pixel cycle conversion element.

3. A radiographic apparatus, according to claim 1, wherein:
    said line deficiency correction element is operative, during a use of said radiographic apparatus, to obtain a pixel of the same phase as the line deficiency pixel in the moire pattern on each line from a number of pixels in said one (1) cycle of the moire pattern obtained on each line orthogonal to said lines of said moire pattern appearing in said X-ray image during said use; and
    said line deficiency correction element being operative, during said use, to correct a line deficiency pixel value of each line by using the pixel value of the same phase as the line deficiency pixel obtained on each line.

4. A radiographic apparatus, according to claim 1, further comprising:
    a pixel extraction element operative to extract a preset and a predetermined number of pixels from pixels orthogonal to the lines of the moire pattern appearing in said X-ray image, and
    said Fourier transform element operative to conduct a one-dimensional Fourier transform on the pixels extracted by said pixel extraction element.

5. A radiographic apparatus, according to claim 1, further comprising:
    a moire pattern elimination processing element operative to conduct a processing to eliminate a moire pattern from said X-ray image, wherein the line deficiency is corrected.

6. A radiographic apparatus, according to claim 5, further comprising:
    a peak frequency detection element,
    wherein said moire pattern elimination processing element is operative to eliminate a moire pattern from said X-ray image based on a peak frequency detected by said peak frequency detection element.

7. A method for operating a radiographic apparatus, to correct an X-ray image during a use, said method for operating comprising the steps of:
    providing a radiation element and irradiating with X-rays an external subject during said use;
    providing an X-ray detector and detecting said X-rays passing through the subject;
    providing an X-ray grid set in an X-ray incident side of said X-ray detector and eliminating scattered lines;
    operatively providing a Fourier transform element and conducting a one-dimensional Fourier transform on a line orthogonal to a line of a moire pattern appearing in said X-ray image, said one-dimensional Fourier transform having a result;
    operatively providing a peak frequency detection element and detecting a peak frequency from the result of said one-dimensional Fourier transform;

operatively providing a pixel cycle conversion element and converting said peak frequency to a number of pixels in one (1) cycle of said moire pattern; and operatively providing a line deficiency correction element and obtaining pixels of the same phase as line deficiency pixels in said moire pattern from the number of pixels in said one (1) cycle of said moire pattern, and correcting said line deficiency pixel by using the pixel value of the obtained pixels.

8. A method for operating a radiographic apparatus, according to claim 7, further comprising the step of:

operating said pixel cycle conversion element with a conversion table.

9. A method for operating a radiographic apparatus, according to claim 7, further comprising the steps of:

operating said line deficiency correction element to obtain a pixel of the same phase as the line deficiency pixel in the moire pattern on each line from a number of pixels in said one (1) cycle of the moire pattern obtained on each said line orthogonal to said lines of said moire pattern appearing in said X-ray image during said use; and operating said line deficiency correction element to correct a line deficiency pixel value of each line by using the pixel value of the same phase as the line deficiency pixel obtained on each line.

10. A method for operating a radiographic apparatus, according to claim 7, further comprising the steps of:

providing a pixel extraction element;

operating said pixel extraction element to extract a preset and predetermined number of pixels from pixels orthogonal to said lines of said moire pattern appearing in said X-ray image; and using said Fourier transform element to conduct a one-dimensional Fourier transform on said pixels extracted by said pixel extraction element.

11. A method for operating a radiographic apparatus, according to claim 7, further comprising the steps of:

providing a moire pattern elimination processing element; and operating said moire pattern elimination processing element to eliminate a moire pattern from an X-ray image thereby correcting a line deficiency.

12. A method for operating a radiographic apparatus, according to claim 11, further comprising the steps of:

operating said moire pattern elimination processing element to eliminate said moire pattern from said X-ray mage based on a peak frequency detected by said peak frequency detection element.

* * * * *